(12) United States Patent
Dourdeville

(10) Patent No.: US 7,128,081 B2
(45) Date of Patent: Oct. 31, 2006

(54) PELTIER BASED FREEZE-THAW VALVES AND METHOD OF USE

(75) Inventor: Theodore A. Dourdeville, Marion, MA (US)

(73) Assignee: Waters Investments Limited, DE (US)

( * ) Notice: Subject to any disclaimer, the term of this patent is extended or adjusted under 35 U.S.C. 154(b) by 0 days.

(21) Appl. No.: 11/148,615

(22) Filed: Jun. 9, 2005

(65) Prior Publication Data
US 2005/0236056 A1 Oct. 27, 2005

Related U.S. Application Data

(63) Continuation of application No. PCT/US03/039071, filed on Dec. 9, 2003.

(60) Provisional application No. 60/431,810, filed on Dec. 9, 2002.

(51) Int. Cl.
*F17D 1/18* (2006.01)
*F15C 1/04* (2006.01)

(52) U.S. Cl. .................. 137/13; 137/341; 137/828; 251/251.1

(58) Field of Classification Search ............. 137/828, 137/341, 334, 13; 251/251.1
See application file for complete search history.

(56) References Cited

U.S. PATENT DOCUMENTS

| | | | |
|---|---|---|---|
| 3,074,244 A | 1/1963 | Malaker et al. | |
| 4,220,012 A | 9/1980 | Brister | |
| 4,612,959 A | 9/1986 | Costello | |
| 4,796,430 A | 1/1989 | Malaker et al. | |
| 4,877,434 A | 10/1989 | Malaker | |
| 4,912,932 A | 4/1990 | Malaker et al. | |
| 4,949,742 A | 8/1990 | Rando | |
| 4,989,626 A | 2/1991 | Takagi et al. | |
| 5,101,848 A | 4/1992 | Kojima et al. | |
| 5,119,640 A | 6/1992 | Conrad | |
| 5,705,813 A | 1/1998 | Apffel et al. | |
| 5,716,825 A | 2/1998 | Hancock et al. | |
| 5,795,788 A | 8/1998 | Bevan et al. | |
| 5,988,197 A | 11/1999 | Colin et al. | |
| 6,007,302 A | 12/1999 | Welle | |
| 6,017,693 A | 1/2000 | Yates et al. | |
| 6,041,811 A | 3/2000 | Walter et al. | |
| 6,159,744 A | 12/2000 | Bevan et al. | |
| 6,322,970 B1 | 11/2001 | Little et al. | |
| 6,557,575 B1* | 5/2003 | Gerhardt et al. | ............... 137/13 |
| 6,610,201 B1* | 8/2003 | Dourdeville | ............. 210/198.2 |
| 2001/0039014 A1* | 11/2001 | Bass et al. | ...................... 435/6 |
| 2002/0092363 A1* | 7/2002 | Jorgenson et al. | ....... 73/861.95 |

(Continued)

*Primary Examiner*—A. Michael Chambers
(74) *Attorney, Agent, or Firm*—Brian Michaelis; Anthony J. Janiuk

(57) ABSTRACT

A freeze-thaw valve is provided using a Peltier heat pump where the thermal short-circuit path between a cooled thermal mass and a heated thermal mass is reduced or absent and the valve state transition time is minimized. The freeze-thaw valve comprises a Peltier heat pump mounted to a heat exchange surface that comprises a cross-drilled copper water jacket or manifold. The Peltier heat pump is operated to maintain a cooled thermal mass at a substantially constant low temperature. A resistance heating element is used to produce a heated thermal mass. The freeze-thaw segment of a fluid conduit is commutated to contact either the heated or the cooled thermal mass to thaw and therefore open the valve or cool and thus close the valve. The operation of the Peltier heat pump at a constant temperature avoids problems inherent in the use of a Peltier heat pump to both heat and cool a freeze thaw segment.

22 Claims, 4 Drawing Sheets

U.S. PATENT DOCUMENTS

2002/0129664 A1* 9/2002 Jorgenson et al. ....... 73/861.95

2002/0150683 A1* 10/2002 Troian et al. ............... 427/256

* cited by examiner

PELTIER BASED FREEZE-THAW VALVES AND METHOD OF USE

CROSS REFERENCE TO RELATED APPLICATIONS

This application claims benefit of and is a continuation of International Application No. PCT/US03/039071, filed Dec. 9, 2003 and designating the United States, which claims benefit of and priority to U.S. Provisional Application No. 60/431,810, filed Dec. 9, 2002. The entire contents of these applications are incorporated herein by reference.

FIELD OF THE INVENTION

This invention relates generally to freeze-thaw valve technologies that are capable of performing a high-pressure isolation function.

BACKGROUND OF THE INVENTION

The management of the flow of liquids within small diameter channels presents challenges as the scale of the channels and volumes of the liquids are reduced. One significant constraint is the configuration of traditional valve technology. The management of liquid flows in nano-liter volumes encounters significant limitation when the scale of fluid management is severely affected by poorly-swept or dead volume that is inherent within traditional switching methods. The method of using fluid within these nano scale capillaries and channels to act as its own on/off valve by freezing and thawing that liquid is known in the art, see for example U.S. Pat. Nos. 6,159,744 and 5,795,788. It has been found that the flow of liquids can be diverted to a further channel or chamber by merely freezing and thawing the liquid contained within a segment of tubing or channel. This flow-switching device, which is referred to as "freeze-thaw valving", requires no moving parts within the solvent-wetted path and most importantly contributes no dead volume within the analytical system.

Prior art freeze-thaw valves freeze liquid within a freeze-thaw segment by aspirating a jet of cold gas directly at the freeze-thaw segment. Agents such as liquid carbon dioxide and liquid nitrogen have been used to freeze the contents of the freeze-thaw segment. Unfortunately, the aspiration of the jet of cold gas at the freeze-thaw segment can lead to a build up of frost that acts as insulation, reducing the efficiency of refrigeration and allowing the temperature within the freeze-thaw segment to rise. This elevated temperature, within the freeze-thaw segment, results in the eventual failure of the valve. Additionally, a large volume of gas is needed to operate these prior art freeze-thaw valves.

While prior art freeze-thaw valves utilized a jet of cold gas directed at a freeze-thaw segment, heat pumping based on Peltier principles is a viable method of heat removal to accomplish freezing of the liquid contents of the freeze-thaw segment. Typically, a cascade or series-arrangement of Peltier stages is necessary to attain the required temperatures for rapid freezing of the freeze-thaw segment. Commercially available six-stage cascades are capable of producing temperature differentials as high as 130 degrees Centigrade between the respective hot and cold faces of the heat pump. Unfortunately, such cascades typically do not respond rapidly enough when a drive voltage is applied, because in order to change temperature they must transfer heat associated with their own thermal mass. Additionally, when rapid and/or large-magnitude changes are made in device temperature, thermal stresses induced by such changes contribute to degradation of the device and shortening of device lifespan.

In order to avoid thermal stress problems in Peltier heat pumps used for freeze-thaw valving, it is desirable to operate the heat pump in a mode where it is driven with a substantially constant drive current causing the resulting temperature differential between the hot and cold faces to be substantially constant. Unfortunately, the operation of a Peltier heat pump in a constant pumping mode is not conducive to its use in freeze-thaw valving, because in order to properly utilize freeze-thaw valving it is necessary to be able to both freeze and thaw the same selected segment of a fluidic conduit.

SUMMARY OF THE INVENTION

The present invention provides a freeze-thaw valve using Peltier heat pump refrigeration where the Peltier device is constantly energized and where the valve state transition time (OPEN to CLOSED or CLOSED to OPEN) is minimized.

According to the invention, a freeze-thaw valve comprises a Peltier stack mounted to a heat exchange surface that includes a cross-drilled copper water jacket or manifold. The water jacket removes unwanted heat that is pumped through the Peltier stack, including the joule heat that results from the electrical drive of the Peltier elements. The water jacket is typically one component of a liquid circulation heat rejection path that includes a radiator and circulation pump. In an alternative embodiment a finned heat sink that is air cooled is used to remove the unwanted heat from the Peltier stack.

On the cold face of the Peltier stack, a cooled thermal mass is attached and is oriented with respect to a heated thermal mass with a small intervening gap through which is located a freeze-thaw segment of a fluidic conduit carrying the liquid to be frozen. The heated thermal mass is heated by a resistive heating element to maintain a temperature above the melting point of the liquid. Both the cooled thermal mass and the heated thermal mass are configured from material having a good thermal conductivity. The fluidic conduit is in intimate thermal contact with a movable low mass block having a high thermal conductivity. This low mass block, containing the fluidic conduit, can be moved alternately between contact with the heated mass and contact with the cooled mass. The relatively low thermal mass of the movable block coupled with high thermal conductivity allow its temperature to change rapidly when it is moved from a position contacting the heated or cooled thermal masses. This ability to rapidly change temperature by commutating the position of the movable block allows the freeze-thaw valve to be opened or closed within a short period of time without imposing large cyclic thermal stresses upon the Peltier stack.

In an alternative embodiment, the freeze-thaw valve according to the invention is housed within an enclosure, the interior of which is maintained under partial vacuum conditions. Evacuation of air and associated water vapor substantially eliminates frost buildup on the cold surfaces of the valve. High-quality vacuum can be further utilized to significantly reduce that component of heat transfer between the heated and cooled regions of the valve which is attributable to conduction and convection by air. The absence of air allows the enclosure, within this illustrative embodiment, to be constructed from materials having good thermal conductivity. The fabrication of the enclosure from a material having good thermal conductivity allows it to be used as a thermal circuit that thermally links the hot face of the Peltier heat pump with the heated thermal mass. The linkage of these two components allows the transfer of heat from the Peltier hot face to the heated thermal mass and dispenses with the need to heat the heated thermal mass with resistive heating elements.

In yet a further illustrative embodiment, a fluidic conduit having a freeze thaw segment is cradled within a channel upon a cold face of a Peltier heat pump. The Peltier heat pump is operated at a substantially constant cold-face temperature. The cradle has a thermal bridge having several voids between the freeze-thaw segment and the Peltier cold face. To "open" the freeze-thaw valve heat is applied to the freeze-thaw segment by a resistive heating element. The applied heat opposes the constant cooling provided by the heat pump. When heat is no longer applied to the fluidic conduit, the surrounding thermal mass of the channel region cools rapidly because of heat flow through the thermal bridge to the Peltier cold face. The cooled channel region freezes the contents of the fluidic conduit "closing" the freeze-thaw valve.

The freeze-thaw valves according to the invention may be employed as simple isolation valves that protect other system components from extremes of pressure or they may be configured to create higher-order subsystems such as micro or nano-scale sample injectors or sample trapping subsystems.

Advantages of the valves according to the invention include the avoidance of repetitive cyclic thermal stresses to the Peltier device and resulting shortened lifespan by the ability to operate the Peltier heat pump at a substantially constant heat pumping rate. Additionally, the use of a constant cold-face temperature together with the commutating of the freeze-thaw segment to either the hot or cold thermal mass of the device avoids the slow response time associated with the thermal mass of the Peltier heat pump and allows for valve transition time to be minimized. The inventive freeze thaw valve also does not require a large consumable external cooling source such as in the prior art and therefore the use of the inventive freeze-thaw valve is permissible within smaller analytical devices. Further, the operation of the device within a vacuum enclosure avoids the frost buildup and subsequent failure of the freeze-thaw valve.

BRIEF DESCRIPTION OF DRAWINGS

These and other features and advantages of the present invention will become apparent from the following detailed description taken in conjunction with the accompanying drawings that illustrate the exemplary embodiments of the method and apparatus for freeze-thaw valving of the present invention.

DETAILED DESCRIPTION

Figure 1:
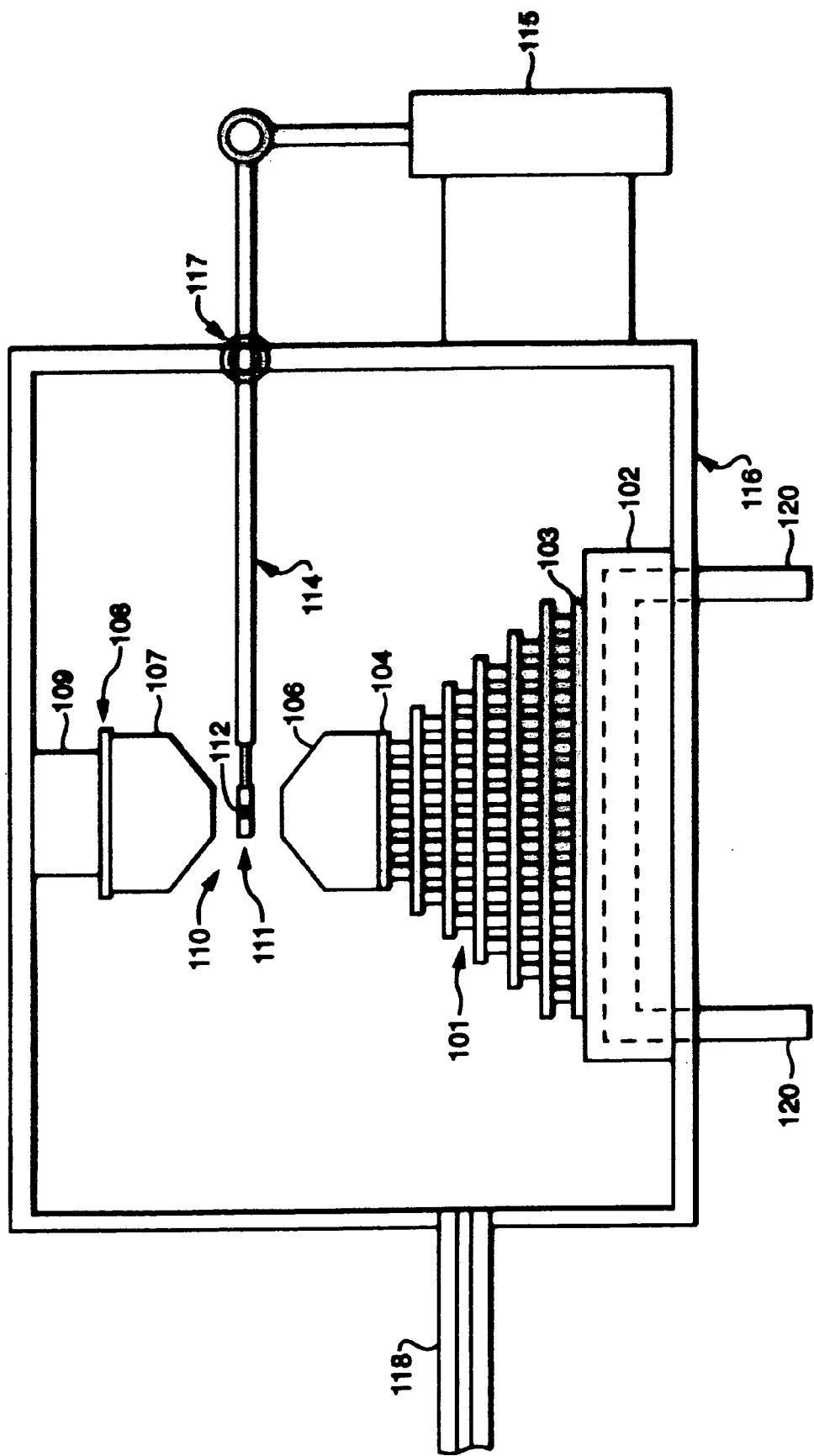
FIG. 1 is a schematic of a commutating freeze-thaw valve that is cooled by a Peltier heat pump according to the invention.

Turning to FIG. 1, an illustrative freeze-thaw valve according to the invention is shown. This illustrative freeze-thaw valve is cooled by a Peltier stack 101 having a hot face 103 and a cold face 104. The hot face 103 of the Peltier stack 101 is mounted to a heat exchange surface 102. The heat exchange surface 102 is comprised of a cross-drilled copper water jacket or manifold. This heat exchange surface 102 allows heat to be removed from the hot face 103 of the Peltier stack 101 that results from both the useful heat pumping and power dissipation within the electrical drive elements within the Peltier stack 101. The water jacket contained within the heat exchange surface 102 is typically one component of a liquid circulation path having a small radiator and circulation pump. The circulation path connects to the water jacket at coolant ports 120. The cold face 104 of the Peltier stack 101 is affixed to a cooled thermal mass 106. The cooled thermal mass 106 is configured from materials having good thermal conductivity.

A heated thermal mass 107 is oriented opposite the cooled thermal mass 106. The heated thermal mass 107 is configured from material having good thermal conductivity and is heated by a resistive heating element 108. The resistive heating element 108 is affixed to the heated thermal mass 107 and causes it to be heated to a temperature above the melting point of the mobile phase to be valved. Both the heated thermal mass 107 and the resistive heating element 108 are positioned and affixed within the illustrative embodiment by the use of a mounting block 109. The mounting block 109 is configured from materials having sufficient strength and poor thermal conductivity. The two thermal masses 106 and 107 are typically constructed from materials having good thermal conductivity, such as copper. Other materials having sufficient strength and thermal conductivity as known by those skilled in the art may be used.

The thermal masses 106 and 107 are positioned opposite each other and are separated by an intervening gap 110. The intervening gap 110 is of sufficient size to allow a commutating block 111 to move from the cooled thermal mass 106 to the heated thermal mass 107 or vice versa. The commutating block 111 is configured from materials having high thermal conductivity, and is dimensioned to provide a relatively low thermal mass. In one illustrative embodiment the commutating block 111 is fashioned from aluminum. Other materials may be used that have low mass and high thermal conductivity. The commutating block 111 contains within it a channel (not shown) that houses a fluidic conduit 112. This fluidic conduit 112 carries a mobile phase that is either frozen or thawed to close or open the freeze-thaw valve. The fluidic conduit 112 can have a consistent interior cross-section or it can utilize various geometries and shapes as shown in U.S. Pat. No. 6,557,575 to Gerhardt et. al., which is incorporated in its entirety by reference. The fluidic conduit 112 is mounted within the channel in intimate thermal contact within the movable block 111. This intimate thermal contact can be achieved by either a small mechanical clearance dimension between the channel and fluidic conduit 112 or the use of a thermally-conductive potting compound.

The commutating block 111 is transported between polar positions in contact with either thermal mass 106, 107. The transporting of the commutating block 111 is controlled by an actuating arm 114. The actuating arm 114 is configured from material having low thermal conductivity and mass. The movement of the actuating arm 114 is provided by a solenoid actuator 115 or it can also be accomplished by an air cylinder, linear motor or other devices known to those skilled in the art. The solenoid actuator 115 or other drive mechanisms are typically located away from and outside an enclosure 116 containing the above device. The enclosure 116 prevents humidity, present in ambient air, from condensing and freezing upon the cooled regions of the freeze-thaw valve. Typically the actuating arm 114 is connected to its driving mechanism located outside the enclosed assembly through a flexible-sealable opening 117 within the enclosure 116.

The enclosure 116 is provided with a pumping port 118 that allows connection with a roughing vacuum. The use of a roughing vacuum ensures that no liquid-phase water accumulates anywhere within the assembly and it also ensures that surfaces warmer than approximately −25° C. remain free of ice. At extremely cold temperatures (−30° C. to −80° C.) the vapor pressure of ice is sufficiently low that roughing vacuum will not cause ice to sublimate. Therefore, in order to defrost the assembly it is necessary that cold surfaces within the assembly be transiently elevated to a temperature equal to or higher than −25° C. These elevated temperatures allow any ice formation to sublimate away.

In an alternative embodiment, a higher quality vacuum substantially eliminates thermal conduction and convection by air internal to the enclosure 116. The use of a higher quality vacuum substantially eliminates air from the enclosure 116. The absence of air allows the enclosure 116, within this alternative embodiment, to be constructed from materials having good thermal conductivity. The fabrication of the enclosure 116 from a material having good thermal conductivity allows it to be used as a thermal circuit that thermally links the hot face 103 of the Peltier stack 101 with the heated thermal mass 107. The linkage of these two components allows the transfer of heat from the hot face 103 of the Peltier stack to the heated thermal mass 107 and dispenses with the need to heat the heated thermal mass 107 with the resistive heating element 108. In this configuration, mounting block 109 would be constructed from a thermally-conductive material.

Figure 2:
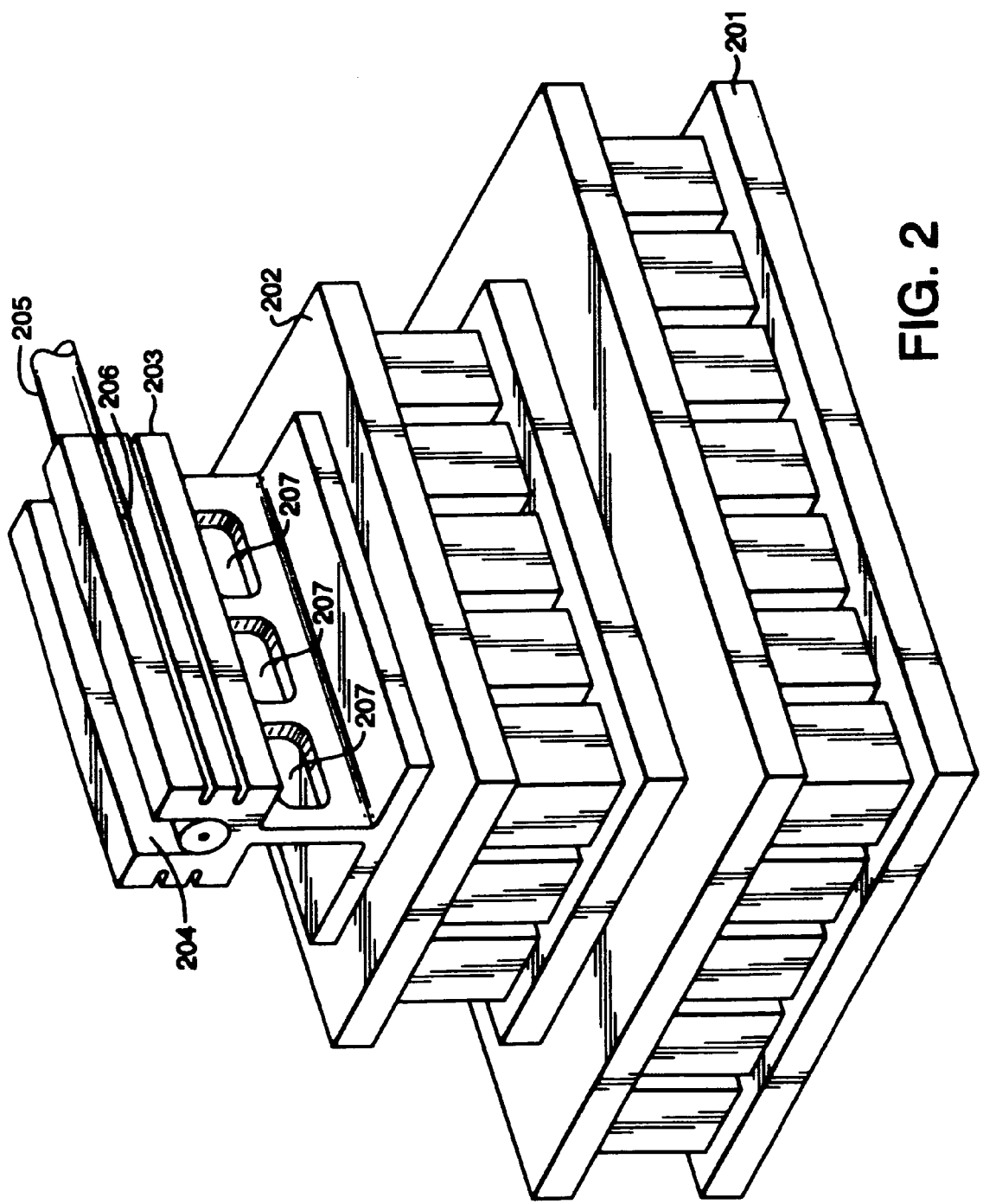
FIG. 2 depicts a Peltier based freeze-thaw valve that is operated at a constant cooled temperature and thawed by resistance heating according to the invention.

A further alternative embodiment, using a Peltier heat pump for cooling within a freeze-thaw valve, is shown in FIG. 2. The Peltier heat pump, within this illustrative embodiment, is a multi-tiered cascade assembly having approximately two to five stages, of which only the top stage or coldest face is shown. The use of these multiple stages allows sufficiently low temperatures to be achieved at the cold face of the Peltier heat pump (typically about −60 to about −80 degrees Centigrade). The cascade of Peltier devices places the individual stages in a thermal series, such that the temperature differentials generated across the respective stages are substantially additive. The multiple stages of this illustrative embodiment may be connected in parallel or in series depending upon the freeze temperature requirement and the characteristics of the power supply. The Peltier stack has a hot face 201 and a cold face 202. The cold face 202 has mounted upon it a cradling structure 203 that is configured from a thermally conductive material, such as aluminum. Other materials as known to those skilled in the art, having proper thermal conductivity, may be used. The cradling structure 203 contains a channel 204 that receives a fluidic conduit 205 such as a fused silica capillary. Heat rejection from the hot face 201 can be accomplished with a water jacket as part of a liquid cooling loop, as shown in FIG. 1.

The fluidic conduit 205 is in intimate thermal contact with the cradling structure 203. This intimate thermal contact can be achieved by dimensioning the channel 204 in relation to the fluidic conduit 205 therefore causing it to be in intimate thermal contact with the cradling structure 203. Alternatively, the intimate thermal contact can be achieved by the use of a thermally conductive potting compound. The fluidic conduit 205 passing through the cradling structure 203 contains a freeze-thaw segment. The freeze-thaw segment is that area of the fluidic conduit 205 that is frozen or thawed to close or open the valve. The outside area of the cradling structure 203, adjacent to the fluidic conduit 205, has a plurality of grooves 206 running the length of the freeze thaw segment that allow for the insertion of a resistive heating element such as a Formvar-insulated nichrome wire.

In the operation of this illustrative embodiment, the cold face 202 of the Peltier heat pump is maintained at a constant temperature that is significantly below the freezing point of the mobile phase used within the analytical device. Operating the Peltier heat pump at this constant temperature avoids repetitive thermal stresses that can occur when a device is required to cycle up and down to achieve heating and cooling. Further, operating at a constant temperature improves the response time of the valve, as the cool-down rate of the Peltier heat pump does limit or impact the performance of the valve actuation cycle.

In this illustrative embodiment, to "open" the freeze-thaw valve heat is applied to a localized region around the freeze-thaw segment by the resistive heating elements. The applied heat opposes the constant cooling of the cold face 202 by the Peltier heat pump and causes the mobile phase within the fluidic conduit 205 to thaw and flow. The applied heat results in a significant temperature differential across the median web of the cradling structure 203, and therefore the cradling structure 203 is fitted with several voids 207, within the median web, in order to control the cross-section available for heat flow.

When heat is no longer applied to the fluidic conduit 205, the surrounding thermal mass of the channel region cools rapidly because of heat flow through the median web to the base of the cradling structure 203 that is in thermal contact with the cold face 202 of the Peltier heat pump. The thermal mass of the cradling structure 203 is small enough to keep the speed of actuation of the freeze-thaw valve high. While the thermal resistance through the median web needs to be sufficiently low to obtain rapid cooling of the channel region, it should not allow a large heat load to be imposed by the resistive heating of cradling structure 203 upon the Peltier heat pump.

Figure 3:
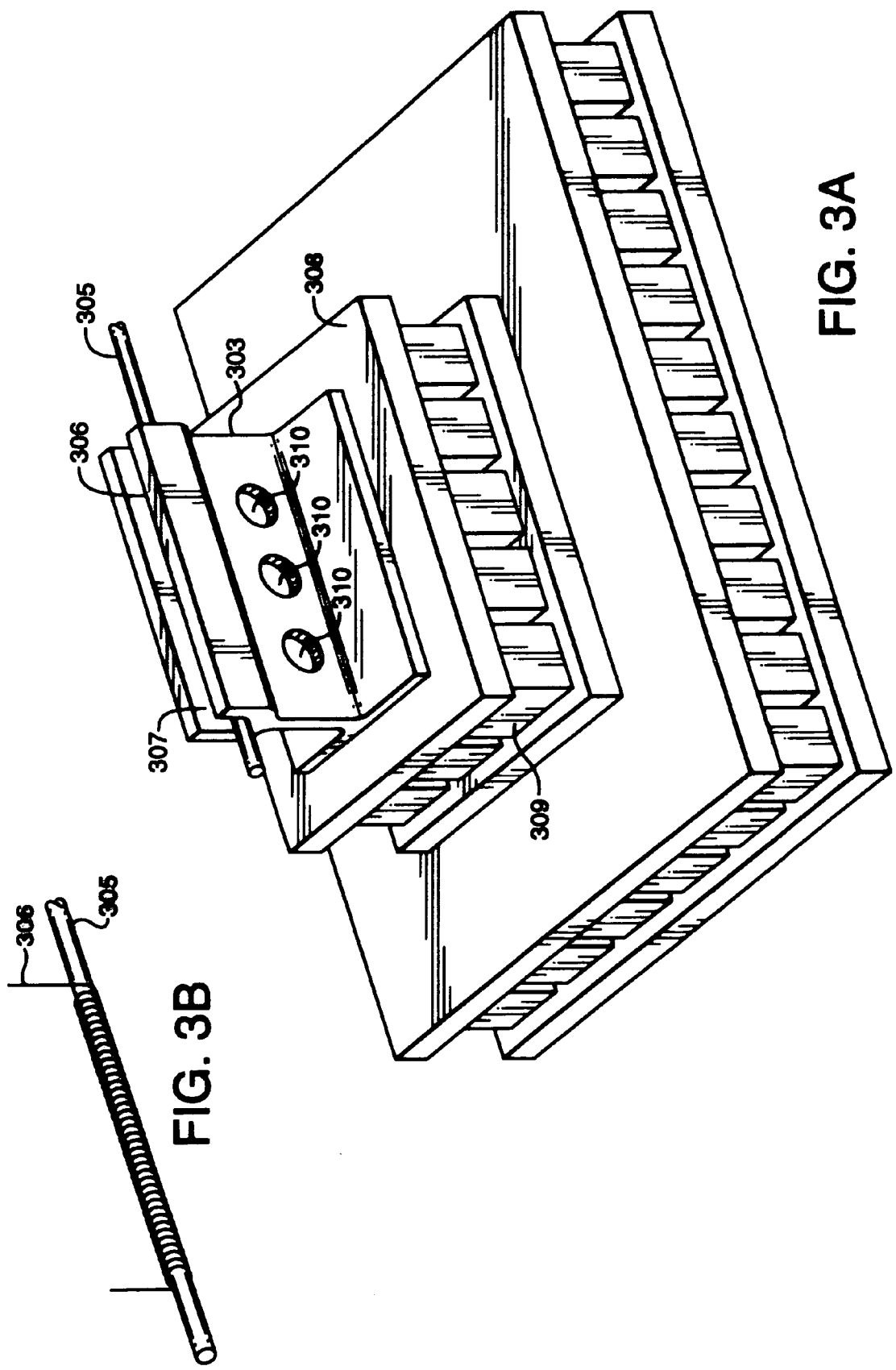
FIGS. 3A and 3B depicts a Peltier based freeze-thaw valve having an alternative method of thawing according to the invention.

Turning to FIGS. 3A and 3B, an alternative approach to thawing the contents of a fluidic conduit 305 is shown. In this illustrative embodiment, a resistance heating wire 306 is wrapped around the fluidic conduit 305. The resistance heating wire 306 is wrapped at least once around the fluidic conduit 305. Alternatively, the function of the resistance heating wire 306 is served by an electrically-heatable resistance film deposited onto or bonded to the fluid conduit 305. The wrapped fluidic conduit 305 is then placed in intimate thermal contact within a cradling structure 303. This intimate thermal contact can be achieved by the precise machining of a channel 307 within the cradling structure 303 or by potting the wrapped fluidic conduit 305 within the channel 307 using a thermal conductive potting compound. The cradling structure 303 rests upon a cold face 308 of a Peltier pump 309. It is contemplated within the scope of the invention, that the Peltier pump 309 may comprise multiple stages (not shown).

In this illustrative embodiment, to "open" the freeze-thaw valve heat is applied to the fluidic conduit 305 by passing an electric current through resistance heating wire 306. The applied heat opposes the constant cooling of the cold face 308 by the Peltier heat pump 309 and causes the mobile phase within the fluidic conduit 305 to thaw and flow. The applied heat results in a significant temperature differential across the median web of the cradling structure 303, and therefore the cradling structure 303 is fitted with several voids 310, within the median web, in order to control the cross-section available for heat flow.

When heat is no longer applied to the fluidic conduit 305, the surrounding thermal mass of the channel region cools rapidly because of heat flow through the median web to the base of the cradling structure 303 that is in thermal contact with the cold face 308 of the Peltier heat pump 309. The thermal mass of the channel 307 region of the cradling structure 303 is small to keep the speed of actuation of the freeze-thaw valve high. While the thermal resistance through the median web needs to be sufficiently low to obtain rapid cooling of the channel region, it should not allow a large heat load to be imposed by the resistance heating wire 306 upon the Peltier heat pump 309.

The Peltier based freeze-thaw valves according to the invention can be incorporated into a variety of different micro- or nano-scale devices to achieve valving of the mobile phase of any such device. Specifically, the Peltier based freeze-thaw valve is useful in a microfluidic-scale sample trapping subsystem.

Figure 4:
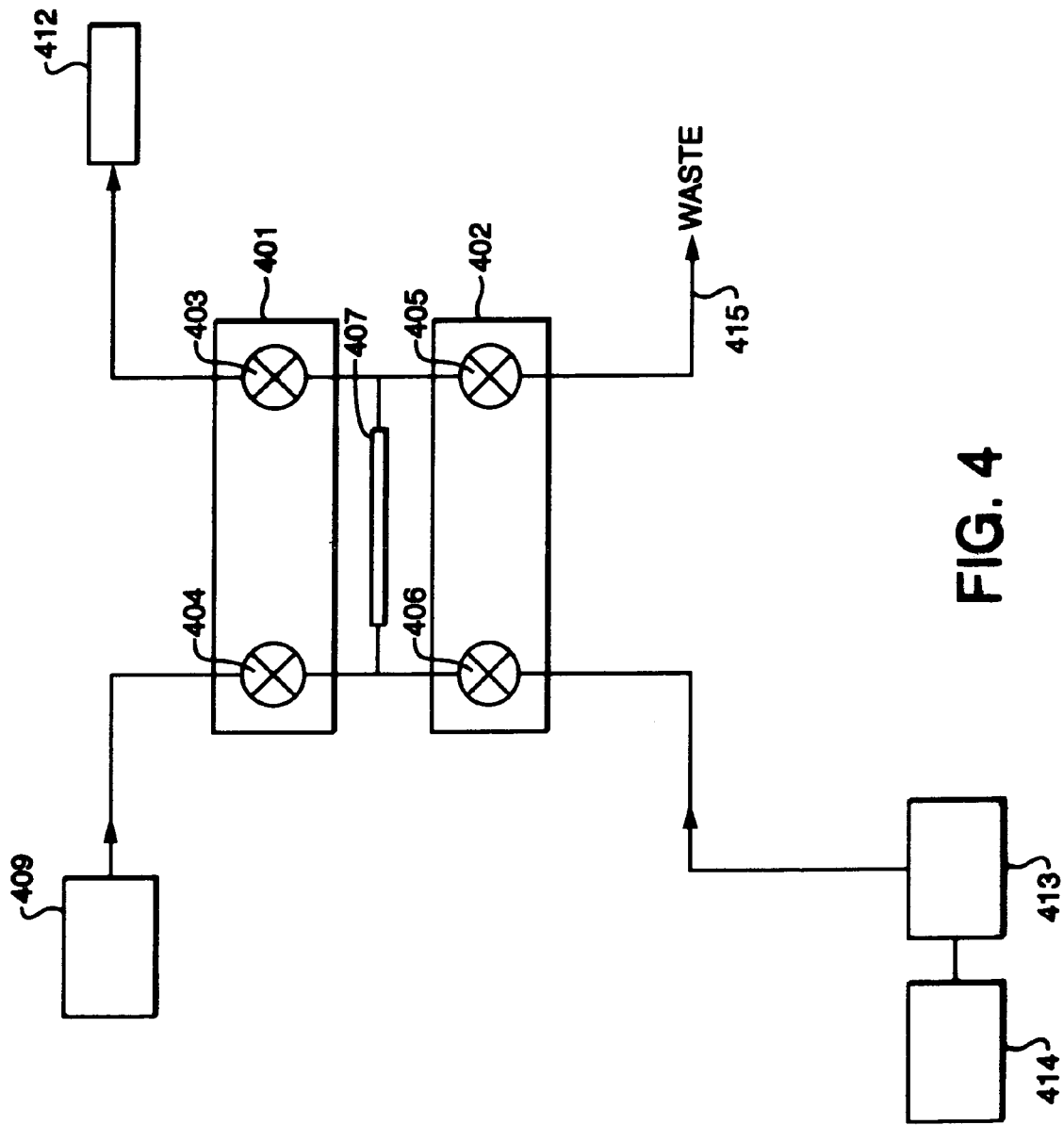
FIG. 4 is a schematic of a micro-fluidic sample trapping subsystem utilizing a Peltier heat pump for cooling according to the invention.

Turning to FIG. 4, a schematic of a sample trapping subsystem for use with a caisson-based LC separation system is shown. The caisson-based LC separation system is the subject of U.S. Pat. No. 6,610,201 to Dourdeville, which is incorporated in its entirety by reference. The Peltier-based freeze-thaw valves allow the introduction of sample onto a trapping column at relatively low pressure, and subsequently allow the elution of that sample at very high pressure, while isolating the sample injector and trapping pump from exposure to the high elution pressure.

The sample trapping subsystem is fluidically connected between a caisson pump 409 and an analytical column 412. The sample trapping subsystem has multiple freeze-thaw valves within a first sub-region 401 and a second sub-region 402. The first sub-region 401 contains a first pair of freeze-thaw valves comprised of a first freeze-thaw valve 403 and a second freeze-thaw valve 404. The second sub-region 402 contains a second pair of freeze-thaw valves comprised of a third freeze-thaw valve 405 and a fourth freeze-thaw valve 406. Valve pairs within each of sub-regions 401,402 are controlled so as to freeze and thaw substantially simultaneously. The two sub-regions 401,402 are capable of independent actuation. The freeze-thaw valves within sub-regions 401 and 402 can utilize independent Peltier cascades, or can share refrigeration from a single cold surface. The trapping column 407 resides between the first sub-region 401 and the second sub-region 402. The trapping column 407 resides away from the cold surfaces of the two sub-regions 401, 402 so that its contents are not subject to freezing that could give rise to sample precipitation or other undesired effects.

When the first sub-region 401 is frozen resulting in the first valve 403 and second valve 404 being closed and the second sub-region 402 is thawed resulting in the third valve 405 and the fourth valve 406 being opened, the trapping column 407 is in fluid communication with sample injector 413 and waste path 415. In this condition, an injected sample can be pumped onto trapping column 407 by the liquid delivery of trapping pump 414. Trapping flow delivery is maintained until the full sample volume has been delivered through trapping column 407, and until any necessary additional flushing or sample washing has been accomplished.

In the alternate state, the second sub-region 402 is frozen resulting in the third 405 and fourth 406 valve being closed, and the first sub-region 401 is thawed resulting in the first 403 and second 404 valves being opened. In this state, the sample injector 413, trapping pump 414, and waste path 415 are isolated from the chromatographic elution path. This isolation allows caisson pump 409 to bring about elution of sample from trapping column 407, and subsequently from analytical column 412, at pressures well above the pressure capabilities of the sample injector 413 and trapping pump 414. The pressure isolation obtained by freeze-thaw valving significantly simplifies the overall system design by limiting the number of components exposed to the analytical chromatography pressure. Further, that pressure isolation is obtained without the introduction of unswept volumes or additional sealing materials into the wetted path.

Although the illustrative freeze thaw valves of the present invention are described in connection with their use in an analytical system such as those used in high performance liquid chromatography (HPLC), capillary liquid chromatography (capillary LC), and capillary electrophoresis (CE), it is within the scope of the present invention for a freeze-thaw valve having the same basic construction as herein described to be used within any configurations where freeze thaw valving would be advantageous.

Although the illustrative freeze-thaw valves of the present invention are described in connection with their use in a micro-fluidic sample trapping subsystem, it is within the scope of the present invention for a freeze-thaw valve having the same basic construction as herein described to be used within configurations suitable for direct sample injection into an analytical system without trapping. Likewise, it should be appreciated that the freeze-thaw valves according to the present invention could be utilized within any micro, nano or meso scale apparatus where the use of freeze-thaw valving would be advantageous.

Although the freeze-thaw valves of the present invention are described as having singular freeze thaw segments upon a cold face or commutated to a cold face, it should be appreciated that multiple freeze-thaw segments can be grouped within a singular cold face of a Peltier heat pump. Likewise, the thawing of freeze-thaw segments can also be achieved in multiple groupings.

Although one illustrative embodiment of the freeze-thaw valve of the present invention is described as commutating the freeze-thaw segment to either hot or cold faces, it should be further appreciated that the freeze-thaw segment can be stationary having the hot and cold faces commutating to its location.

Various other changes, omissions and additions in the form and detail of the present invention may be made therein without departing from the spirit and scope of the invention. Therefore, the above description should not be construed as limiting, but merely as exemplification of the various embodiments.

What is claimed is:

1. A method of controlling the flow of a fluid comprising the steps of:
   a. providing a housing having a heated thermal mass at a first position and a cooled thermal mass at a second position, said heated thermal mass oriented with respect to said cooled thermal mass at a second position with an intervening gap;
   b. providing a movable block having a channel, said channel being capable of receiving a fluidic conduit, said movable block located in said intervening gap and, said fluidic conduit capable of transporting one or more fluids, freezing the fluids contained therein at a low temperature to restrict flow and thawing fluids contained therein at a high temperature to allow flow;

c. providing a movement means secured to said housing to move said movable block between said first position and said second position, d. actuating said movement means to move said movable block between said first position to restrict flow and said second position to allow flow.

2. The method of claim 1 wherein said movable block is of low thermal mass.

3. The method of claim 1 wherein said movable block is moved by an actuating arm.

4. The method of claim 1 wherein said heated thermal mass is heated by resistance heating.

5. The method of claim 1 wherein said cooled thermal mass is cooled by the cold face of a Peltier heat pump.

6. The method of claim 5 wherein said Peltier heat pump is maintained at a substantially constant temperature.

7. The method of claim 6 wherein said heated thermal mass is heated by means of a thermal circuit linking said heated thermal mass with hot face of said Peltier heat pump.

8. The method of claim 5 wherein said housing is maintained under vacuum.

9. A device for controlling the flow of fluid comprising:
a housing having a heated thermal mass at a first position and a cooled thermal mass at a second position, said heated thermal mass oriented with respect to said cooled thermal mass at a second position with an intervening gap;
a movable block having a channel, said channel being capable of receiving a fluidic conduit, said movable block located in said intervening gap, said fluidic conduit capable of transporting one or more fluids, freezing the fluids contained therein at a low temperature to restrict flow and thawing fluids contained therein at a high temperature to allow flow;
movement means secured to said housing to move said movable block between said first position and said second position,
wherein at said first position said movable block is in thermal contact with said cooled thermal mass and said fluidic conduit is maintained in a low temperature closed state and wherein in said second position said movable block is in thermal contact with said heated thermal mass and said fluidic conduit is maintained in a high temperature open state.

10. The device of claim 9 wherein said movable block is of high thermal conductivity.

11. The device of claim 9 wherein said movable block if of low thermal mass.

12. The device of claim 9 wherein said movement means is an actuating arm.

13. The device of claim 1 wherein said heated thermal mass is heated by resistance heating.

14. The device of claim 9 wherein said heated thermal mass is heated by the hot face of a Peltier heat pump.

15. The device of claim 9 wherein said cooled thermal mass is cooled by the cold face of a Peltier heat pump.

16. The device of claim 9 wherein said housing is airtight.

17. The device of claim 16 wherein the internal volume of said housing is maintained under vacuum.

18. The device of claim 9 wherein said housing is constructed from a thermally conductive material.

19. The device of claim 18 wherein said housing connects said heated thermal mass and said hot face of a Peltier heat pump.

20. The device of claim 1 wherein said housing has a plurality of moveable blocks.

21. The device of claim 20 wherein said plurality of moveable blocks share one movement means.

22. The device of claim 20 comprises a plurality of movement means.

* * * * *